United States Patent [19]

Tang et al.

[11] Patent Number: 5,215,907

[45] Date of Patent: Jun. 1, 1993

[54] THERMOSTABLE ACID PROTEASE FROM SULFOLOBUS ACIDOCALDARIUS

[75] Inventors: Jordan J. N. Tang; Xin-Li Lin, both of Oklahoma City, Okla.

[73] Assignee: Oklahoma Medical Research Foundation, Oklahoma City, Okla.

[21] Appl. No.: 827,892

[22] Filed: Jan. 30, 1992

Related U.S. Application Data

[63] Continuation of Ser. No. 326,622, Mar. 21, 1989, abandoned, which is a continuation-in-part of Ser. No. 315,618, Feb. 24, 1989, abandoned.

[51] Int. Cl.⁵ ............................................. C12N 9/50
[52] U.S. Cl. .................................... 435/219; 435/220; 435/232
[58] Field of Search .................... 435/219, 220, 232

[56] References Cited

U.S. PATENT DOCUMENTS

| | | | |
|---|---|---|---|
| 3,674,644 | 7/1972 | Yokotsuka et al. | 435/223 |
| 4,442,214 | 4/1984 | Morgan et al. | 435/220 |
| 4,511,490 | 4/1985 | Stanislowski et al. | 435/222 |
| 4,761,374 | 8/1988 | Beppu et al. | 435/232 |

OTHER PUBLICATIONS

Cowan, et al., *Biochem. J.*, 247, 121-133 (1987).
Tang and Wong, *J. of Cellular Biochem.*, 33, 53-63, (1987).

*Primary Examiner*—Johnnie R. Brown
*Assistant Examiner*—Pamela S. Webber
*Attorney, Agent, or Firm*—Kilpatrick & Cody

[57] ABSTRACT

A 46,000 Dalton thermostable, very acidic protease, which has been named thermopsin, was purified to homogeneity from the culture medium of *Sulfolobus acidocaldarius* by a five-step procedure including column chromatographies on DEAE-Sepharose CL-6B, phenyl-Sepharose CL-4B, Sephadex G-100, MonoQ (FPLC), and gel filtration (HPLC). The enzyme is a single polypeptide chain having proteolytic activity over pH range 0 to 11 at temperatures between 0° C. and 100° C., with maximal activity at approximately pH 2 and 90° C. Antibodies directed against thermopsin have been prepared. Through studies using various aspartic protease inhibitors, thiol and metalloprotease inhibitors, and serine protease inhibitors, it was determined that, although similar to some aspartic proteases, the active site of thermopsin is clearly not identical to that of other aspartic proteases. Thermopsin hydrolyses the following bonds: Leu-Val, Leu-Tyr, Phe-Phe, Phe-Tyr, and Tyr-Thr, indicating that the specificity of thermopsin is similar to that of pepsin for the large hydrophobic residues at both sides of the scissile bond. In addition, thermopsin is resistant to detergent inactivation, the protein retaining proteolytic activity even in the presence of high concentrations of sodium dodecyl sulfate.

5 Claims, 4 Drawing Sheets fig. 1 fig. 2 fig. 3b fig. 3a fig. 4

THERMOSTABLE ACID PROTEASE FROM SULFOLOBUS ACIDOCALDARIUS

The U.S. Government has rights in this invention pursuant to National Institute of Health research grant No. AM-01107.

This is a continuation of copending application Ser. No. 07/326,622 filed on Mar. 21, 1989, now abandoned, which is a continuation in part of U.S. Ser. No. 07/315,618, "A Thermostable Acid Protease from *Sulfolobus acidocaldarius*", filed Feb. 24, 1989 by Jordan J. N. Tang and Xin-Li Lin, now abandoned.

BACKGROUND OF THE INVENTION

This invention is generally in the area of enzymes and especially temperature stable enzymes.

Acid proteases are a well established group of proteolytic enzymes which digest proteins and peptides in an acidic solution. Some well known acid proteases are pepsin, gastricsin, chymosin, and cathepsin D. Most of these enzymes share similar amino acid sequences, three-dimensional structures, active-site structures, and catalytic mechanisms. See J. Tang, *Acid Proteases, Structure, Function, and Biology*, (Plenum Press, New York, 1977); V. Kostka, *Aspartic Proteases and Their Inhibitors*, (Walter de Gruyter, Berlin, 1985); and Tang and Wong, *J. Cell. Biochem.*, 33, 53–63 (1987), for a general review of acid proteases. A common property of the active site structures of acid proteases is that these enzymes are inhibited by pepstatin, a transition-state analogue inhibitor, as discussed by Marciniszyn, et al., *J. Biol. Chem.*, 251, 7088–7094 (1976). Because these proteases contain two aspartic acid residues in their catalytic sites, they are also called aspartic proteases. The structure and function relationships of aspartic proteases is a topic of current research interests because some aspartic proteases are involved in diseases, such as renin hypertension and acquired immunodeficiency disease (an acid protease is associated with the maturation of the Human Immunodeficiency Virus), and the availability of high-resolution crystal structures of several aspartic proteases has made these enzymes attractive models for the study of structure-function relationships.

It is therefore an object of the present invention to provide a unique acid protease.

It is another object of the present invention to provide an acid protease having exceptional stability at high temperatures and low pH.

It is a still further object of the present invention provide methods for use of a thermostable, acid stable acid protease.

SUMMARY OF THE INVENTION

A thermostable, acid protease has been isolated from the cells and in the culture medium of *Sulfolobus acidocaldarius*, an archaebacteria. This acid protease, which has been named thermopsin, was purified to homogeneity from the culture medium by a five-step procedure including column chromatography on DEAE-Sepharose CL-6B, phenyl-Sepharose CL-4B, Sephadex G-100, by MonoQ FPLC, and by HPLC gel filtration. The purified thermopsin produces a single band having proteolytic activity when analyzed by SDS-polyacrylamide electrophoresis.

Thermopsin has a molecular weight of approximately $6,300 \pm 4,600$ daltons as determined by gel filtration chromatography. The enzyme is composed of a single polypeptide chain and is very acidic in nature. Purified thermopsin is a good antigen and antibodies directed against the protein have been prepared.

Thermopsin is active over a wide temperature range, between 0° C. and 100° C., and over a wide pH range, between 0 and 11. It has maximal activity at approximately pH 2 and 90° C., but remains stable even at 4° C. and in the pH range of between 8 and 11. The purified thermopsin is also resistant to detergent, the protein retaining proteolytic activity even in the presence of high concentrations (up to 4%) of sodium dodecyl sulfate.

The enzyme activity is strongly inhibited by pepstatin (50% inhibition of activity at 0.5 $\mu$M of inhibitor), suggesting that the protease is similar to other aspartic proteases. However, another aspartic protease inhibitor, diazoacetyl-DL-norleucinemethlyester (DAN), has no effect on thermopsin activity, indicating that the active site of thermopsin is not identical to that of other aspartic proteases. Although classical inhibitors for thiol and metalloproteases have no effect on thermopsin activity, phenylmethylsulfonyl fluoride (PMSF), N-Tosyl-L-phenylalanine chloromethyl ketone (TPCK), antipain, and $NaAsO_2$ produce significant inhibition of proteolytic activity.

The specificity of the proteolytic cleavage sites of thermopsin was studied using a well characterized polypeptide, the oxidized B chain of insulin, as the substrate of the reaction. Insulin B chain was first digested with thermopsin, and the resulting peptide fragments were then isolated and identified. The results demonstrate that the enzyme hydrolyses the following peptide bonds: Leu-Val, Leu-Tyr, Phe-Phe, Phe-Tyr, and Tyr-Thr.

These results indicate that the specificity of thermopsin is similar to that of pepsin, i.e. the enzyme prefers large hydrophobic residues at both sides of the scissile bond. This is confirmed by the cleavage of a synthetic polypeptide substrate, Lys-Pro-Ala-Glu-Phe-Phe(-$NO_2$)-Ala-Leu by thermopsin between Phe and Phe(-$NO_2$). Thermopsin hydrolysis of methylated hemoglobin follows Michaelis-Menten kinetics with an apparent Km of 12 $\mu$M.

DETAILED DESCRIPTION OF THE INVENTION

The present invention is an acid protease, called thermopsin, that is thermostable at higher temperatures, which was isolated from archaebacteria that grow in an acidic environment (approximately pH 2) and at high temperatures (approximately 70° C.). Thermopsin is unusually stable as compared to other aspartic proteases studied to date, including those derived from yeast, fungi, plants, and animal sources, which are thermostable at temperatures below 60° C.

Thermostable acid proteases were detected in the culture medium of thermophilic archaebacteria including *Sulfolobus acidocaldarius*, *Sulfolobus solfataricus*, and *Thermoplasma acidophilum*. The thermostable acid protease isolated from the cells and culture medium of *S. acidocaldarius*, named thermopsin, was purified to homogeneity and characterized for its proteolytic cleavage specificity and enzymatic properties.

Thermopsin is unique among the acid proteases in that it is stable at high temperatures. The activity of the enzyme increases with temperature up to 90° C. The enzyme denatures slowly above this temperature; proteolytic activity, however, is still measurable at 100° C. The low pH optimum (pH 2) and significant pepstatin inhibition suggest that thermopsin is related to the aspartic proteases of the pepsin family. This relationship is further supported by the similarity of the molecular weight of thermopsin (46,300 Daltons) to that of some aspartic proteases such as pepsin (37,000 Daltons). Additionally, the proteolytic specificity studies show that thermopsin is an endopeptidase with preference for large hydrophobic residues at both sides of the scissile bond, which is also a feature shared by many aspartic proteases, such as pepsin, gastricsin, chymosin, and cathepsin D.

There are, however, clear differences between the catalytic apparatus of thermopsin and that of aspartic proteases. Thermopsin is not inactivated by DAN, which inactivates nearly all aspartic proteases. Moreover, the sensitivity of thermopsin activity to inhibition by PMSF, TPCK, and antipain sets it apart from other aspartic proteases. On the basis of the studies with the protease inhibitors, thermopsin is probably an aspartic protease but its active site may contain components reactive to active-site directed (phenyl groups) alkylating reagents. Thermopsin is clearly different from a second group of acid proteases which are pepstatin insensitive (Murao, S. and Oda, K., in Kostka, V. ed. *Aspartic Proteinases and Their Inhibitors*, Walter de Gruyter, Berlin, pp. 379-399 (1985)). Not only is thermopsin pepstatin sensitive, but its molecular weight (46,300 Daltons) is also considerably larger than most of the pepstatin insensitive acid proteases, including the protease B (22,000 Daltons) isolated from *Scytalidium lignicolum* (ATCC 24568), *Lentinus edodes* TMI-563, *Ganoderma lucidum* IFO 4912, *Pleurotus cornucopia*, *Pleurotus ostreatus* IFO 7051, *Flammulina velutipes* IFO 7046, and *Lentinus edodes* IFO 4902 (Marita, T., et al., *J. Biochem.* (Tokyo) 95, 465-475 (1984).

Thermopsin has a variety of pharmaceutical and industrial applications due to its unique properties with respect to broad substrate specificity, low pH optimum, high temperature optimum, and insensitivity to many protease inhibitors. For example, there are many uses in the food industry where it is desirable to have proteases which are active at elevated temperatures, for use in the removal of protein from products, partial digestion of proteins in foods, and to aid in cooking. A particularly desirable application is in the digestion of food and blood stains in clothing washed in hot water, since thermopsin to active both at high temperatures and in the presence of detergent. Pharmaceutical applications include the control and elimination of protein contamination in non-proteinaceous compounds and in contact lens solutions.

Thermopsin can be used in solution, resuspended after lyophilization or freezing, covalently attached to polymeric matrices such as Sephadex, agarose gel beads, and resins, or dispersed in a powder.

Further applications and methods for use therein for thermopsin will be apparent to those skilled in the art from the following detailed description of the isolation and characterization of the enzyme from *S. acidocaldarius*.

Thermopsin was isolated and characterized using the following materials and methods. Materials.

The thermophilic archaebacteria *Sulfolobus acidocaldarius*, *Sulfolobus solfataricus*, and *Thermoplasma acidophilum* were purchased from the American Type Culture Collection (ATCC), Rockville, MD. A synthetic peptide, Lys-Pro-Ala-Glu-Phe-Phe(NO$_2$)-Ala-Leu, was kindly supplied by Dr. I. Blaha (Institute of Organic Chemistry and Biochemistry, Prague, Czechoslovakia). DEAE-Sepharose CL-6B, Sephadex G-100, and phenyl-Sepharose CL-4B were purchased from Pharmacia Fine Chemicals, Piscataway, NJ. $^{14}$C-formaldehyde (specific activity=57.0 mCi/mol) was from New England Nuclear, MA. $^{125}$Iodine was obtained from Amersham. IODOGEN was purchased from Pierce Chemical Co. Oxidized Insulin B chain was purchased from Sigma Chemical Co., St. Louis, MO. Pepstatin, leupeptin, antipain and elastatinal were obtained from Peptide Institute, Inc., Osaka, Japan. Other protease inhibitors were obtained from Sigma Chemical Co. All other reagents were of the highest grade that could be purchased commercially and were used without further purification. Methods.

Large scale culture of *S. acidocaldarius*

*S. acidocaldarius* cells are grown in 35 L of ATCC medium 1256, pH 2, in a 40 L stainless steel container with the temperature regulated at 70° C. Gentle stirring is maintained and oxygen is supplied to the culture by passing a stream of air into the culture medium. Growth is monitored by measuring the absorbance of the culture medium at 540 nm. The cells are normally fully grown in two days. By growing the cells in two containers simultaneously, about 250 L of cell cultures are obtained each week. Due to the extremely low content of thermopsin in the growth medium, very large amounts of culture need to be collected for enzyme purification. A cold shock or cooling of the *S. acidocaldarius* culture from 70° C. to room temperature stimulates the production of thermopsin activity.

Purification of thermopsin from *S. acidocaldarius* culture medium

The cells in 400 L of cell culture are first concentrated using a Millipore pellicon cassette system with a 0.45 μm cassette. The clear filtrate, usually containing 5–10% of the total proteolytic activity, is ultrafiltered to concentrate the protein and exchange the buffer to 20 mM Tris-HCl, pH 8.0. The volume is reduced to 1.5 L using the same pellicon cassette system with a 10,000 Dalton molecular weight cut-off cassette.

The concentrated medium is centrifuged at 16,000 g for 30 min and the clear supernatant applied to a 4.5×32 cm DEAE-Sepharose CL-6B column equilibrated with 20 mM Tris-HCl, pH 8.0. The column is eluted with a linear gradient of 0 to 1M NaCl in 2 L of the same buffer. The active enzyme fractions, which elute at approximately 0.4M NaCl, are pooled. A buffer of 1M sodium formate, pH 3.2, is added to the pooled enzyme solution to a final sodium formate concentration of 0.25M and pH of 3.2. The acidified crude enzyme solution is then incubated at 80° C. for 1 h. SDS-polyacrylamide gel electrophoresis monitoring of the solutions before and after the incubations reveals a significant loss of contaminating proteins, apparently as a result of thermopsin proteolysis.

The enzyme solution is then applied to a 2.5×47 cm phenyl-sepharose CL-4B column, which has been pre-equilibrated with 0.25M sodium formate, pH 3.2. The column is washed first with 4 L of 0.1M sodium formate, pH 3.2, then eluted with 0.1M Tris-HCl, pH 8.0, to recover the enzyme. The enzyme containing eluent is then concentrated to about 10 ml by ultrafiltration in an Amicon apparatus fitted with a membrane to retain molecules having molecular weights above 10,000 Daltons. The buffer of this solution is changed to 0.1M sodium formate, pH 3.2, by several additions of buffer to the ultrafiltration apparatus. This acidic enzyme solution is heated at 80° C. for 1 h, cooled to room temperature, and applied to a 2.5×90 cm Sephadex G-100 column equilibrated and eluted (flow rate: 30 ml/h) with a solution containing 20 mM Tris-HCl, pH 8.0, 50 mM NaCl, and 1% isopropanol. The active fractions from the gel filtration chromatography are pooled and subjected to an anion-exchange chromatography using a MonoQ column in a Pharmacia FPLC (Fast Protein Liquid Chromatography) apparatus. The MonoQ column is equilibrated with 20 mM 1-methylpiperzine, 1% isopropanol, pH 4.5. A linear gradient from 0 to 1M NaCl in 30 min with a flow rate of 1 ml per min is employed for thermopsin elution. The enzyme, which elutes at 0.25M NaCl, is adjusted to pH 3.2 and heated at 80° C. for 1 h. The heated enzyme is subjected to FPLC MonoQ purification one more time. The active fractions are then subjected to final step of purification using HPLC gel filtration on a 7.5×300-mm column (TSK G3000SW) equilibrated and eluted with 0.1M ammonium bicarbonate, pH 8.1.

Proteolytic Assay

Proteolytic activity is routinely assayed using $^{14}C$-methylated bovine hemoglobin as substrate, as prepared according to the method of Lin, et al., *J. Biol. Chem.*, (1989, in press). The assay mixture, containing 0.51% hemoglobin substrate and thermopsin in 0.1 ml of 0.1M sodium formate, pH 3.2, is placed in an Eppendorf tube. After incubation at 80° C. for a period of time between 5 to 30 min, depending on the level of activity of thermopsin used, an aliquot of 0.1 ml of 10% trichloracetic acid is added to stop the reaction and precipitate the protein. After removal of the precipitate by centrifugation, the radioactivity of an aliquot of the clear supernate is determined in a scintillation counter.

SDS-Polyacrylamide Gel Electrophoresis (PAGE)

Proteins are electrophoresed on SDS polyacrylamide gels according to the method of U.K. Laemmli, *Nature* 227, 680–685 (1970) in the presence of mercaptoethanol. The protein samples are incubated with 5% mercaptoethanol in a SDS-containing sample buffer at 100° C. for 5 min prior to electrophoresis.

$^{125}I$-Labeling of Thermopsin

Thermopsin is iodinated according to the methods of Markwell and Fox, *Biochemistry* 17, 4807–4817 (1978) using IODOGEN and $^{125}I$ obtained as referenced above.

Detection of Thermopsin in SDS-PAGE GELS

Thermopsin resists staining with common protein dyes. However, the enzyme can be localized with bovine hemoglobin and Commassie blue at a sensitivity of approximately 0.1 μg. After electrophoresis of thermopsin on SDS polyacrylamide gels, the gel is incubated with 3% hemoglobin, 0.1M sodium formate, pH 3.2 at room temperature for 18 h. The thermopsin-hemoglobin complex is then stained with Commassie blue.

Thermopsin can also be detected on SDS-polyacrylamide gels by its proteolytic activity. Gels are incubated with hemoglobin as described above except that the incubation is at 4° C. for 2 h. Gels are then rinsed with 0.1M sodium formate, pH 3.2, several times and incubated in the same buffer at 40° C. for 17 h. The gels are then stained with Commassie blue to reveal a negatively stained band due to the digestion of hemoglobin by thermopsin.

Molecular Weight Determination

The molecular weight of thermopsin is determined by its chromatographic elution profile on a column of Sephadex G-75 (1.5 ×110 cm) which is equilibrated and eluted with 0.05M sodium acetate, pH 4.0, containing 0.2M NaCl. The position of the enzyme is confirmed by the proteolytic activity of the eluent.

Preparation of antibodies

Polyclonal antibodies directed against purified thermopsin are prepared essentially according to the method of Harlow and Lane, *Antibodies, A Laboratory Manual*, Cold Spring Harbor Laboratory, 1988. For example, each of two adult albino rabbits was injected intradermally with purified thermopsin. The first injection contained 0.1 mg of purified protein suspended in 0.5 ml of Freund's complete adjuvant. After one week each rabbit was injected with 0.1 mg of purified thermopsin suspended in 0.5 ml of incomplete adjuvant. After an additional two weeks the rabbits were again boosted with a third injection of purified protein (0.1 mg) in incomplete adjuvant (0.5 ml). One week after the third injection blood was collected from the marginal veins the rabbits. Additional blood samples were collected at one week intervals.

After clotting, the blood samples were centrifuged and the sera were collected. Ouchterlony double diffusion tests clearly demonstrated that antibodies directed against thermopsin were present in the sera collected from rabbits immunized with the protein.

Monoclonal antibodies are prepared by techniques known to those skilled in the art, for example, the procedure originally developed by Kohler and Milstein (*Nature*, 256:495-497, 1975) and recently described by Harlow and Lane (*Antibodies, A Laboratory Manual*, Cold Spring Harbor Laboratory, 1988), as follows.

A BALB/C mouse is immunized by injection of purified thermopsin. The spleen of the immunized mouse is subsequently removed and dissociated into individual cells. Immunized spleen cells are fused with myeloma cells in the presence of polyethylene to form antibody producing hybridomas. The hybridomas are screened for the production of antibody directed against thermopsin using any of a variety of techniques known to those skilled in the art, such as the Ouchterlony double diffusion technique referenced above. The hybridomas which produce high titers of anti-thermopsin are then injected into mice for the production monoclonal containing ascites fluid, or maintained in culture for the production of culture media containing monoclonal thermopsin antibodies.

FPLC Separation of Peptides

Peptides produced from thermopsin hydrolysis of substrates are chromatographed on a reverse phase column with LC-18 packing (0.26×25 cm, Synchropak RP-P) using a Beckman-Altex HPLC instrument. Two solvents are used: (1) 50 mM potassium phosphate, pH 7.4, and (2) acetonitrile. The separation of peptides is first effected with a linear gradient of 0 to 30% acetonitrile over 20 min followed by isocratic elution with 30% acetonitrile for an additional 15 min. The flow rate is 1.2 ml/min and the peptides are monitored by absorbance at 215 nm.

Kinetic Measurements

Kinetics of thermopsin activity were measured with $^{14}C$-methylated hemoglobin as substrate using the procedures essentially as described above under "Proteolytic Assay". For Km measurements, the incubations were carried out at 80° C. for 5 min in the presence of 1.5% methanol. For studying the pH effects of thermopsin activity, a temperature of 40° C. was used because of the precipitation of hemoglobin at higher temperature at some pH values.

Purification of Thermopsin

Table I compares the total protein, enzymatic activity, specific activity, yield and purification for the material purified from both the culture medium and recovered cells of *S. acidocaldarius*, measured at 80° C. and pH 3.2. Thermostable proteolytic activity of thermopsin was clearly present in both fractions. The activity in the cell fraction, however, appeared to be tightly associated with the cellular structure and was more difficult to purify. The purification of thermopsin, therefore, was carried out using culture media as starting material.

MonoQ FPLC and gel filtration chromatography both produced single elution peaks associated with proteolytic activity, indicating that the enzyme had been purified to homogeneity. Overall, about 2600 fold of purification was achieved with a yield of 13%.

TABLE I

Purification of Thermopsin from 400 L of *S. acidocaldarius* Growth Media

| Steps | Total Protein[a] (mg) | Total Enzyme[b] (mg) | Specific Activity (mg Enz/mg Protein) | Yield (%) | Purification Fold |
|---|---|---|---|---|---|
| Cells | — | 41 | — | — | — |
| Media | 7140 | 2.7 | $3.8 \times 10^{-4}$ | 100 | 1 |
| DEAE-Sepharose | 510 | 2.2 | $4.3 \times 10^{-3}$ | 81 | 11 |
| Phenyl-Sepharose | 70 | 1.4 | $2.0 \times 10^{-2}$ | 52 | 53 |
| Sephadex-G-100 | 26 | 1.1 | $4.2 \times 10^{-2}$ | 41 | 110 |
| FPLC | 0.47 | 0.35 | 0.74 | 13 | 1947 |
| HPLC | 0.35 | 0.35 | 1 | 13 | 2632 |

[a]Measured by absorbance at 280 nm assuming that 1 unit of $A_{280}$ equals 1.2 mg of protein per ml.
[b]Measured by proteolytic activity of thermopsin with purified thermopsin as standard.

The homogeneity of the purified thermopsin was tested by SDS-polyacrylamide gel electrophoresis. Since thermopsin stained poorly with various dyes, the thermopsin was iodinated with $^{125}I$ and then electrophoresed. The autoradiogram of the gel produced essentially a single band. When the gel was soaked in a solution of bovine hemoglobin, the same band could be clearly stained, presumably because of binding of hemoglobin to thermopsin as a substrate. Longer incubation of the gel with hemoglobin followed by incubation at high temperature produced a clearing band at the same electrophoretic position, indicating that hemoglobin had been digested within the area of the band. These results demonstrate the purity and activity of the final thermopsin. Further evidence of homogeneity is the presence of only a single amino-terminal sequence in the purified thermopsin.

Molecular Weight of Thermopsin

The molecular weight of thermopsin from *S. acidocaldarius* was determined to be approximately 46,000 Daltons, based on the elution position of the enzyme from a Sephadex G-75 column and 51,000 Daltons based on its electrophoretic mobility in SDS-polyacrylamide gels. Because of the accuracy in the elution position from the G-75 column, and because other acidic proteins, such as pepsinogen and pepsin, have higher apparent molecular weights than SDS-PAGE would suggest, it is believed that the chromatoqraphy data (46,000 Daltons) is more reliable.

Thermodependence of Thermopsin Activity

Figure 1:
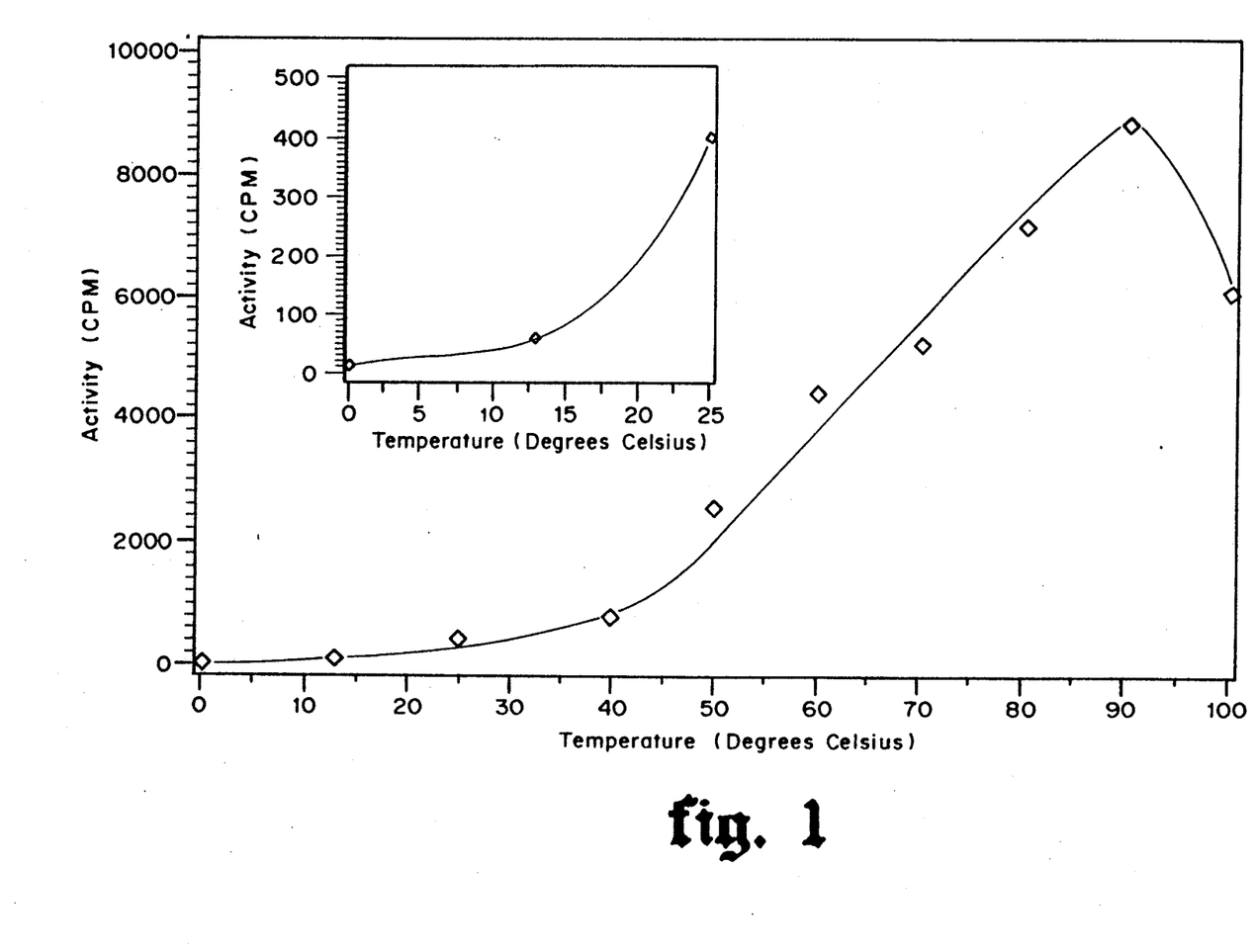
FIG. 1 is a graph of the temperature dependence of the proteolytic activities of thermopsin. The inset of the figure shows the residual activity of thermopsin between 0° C. and 25° C.

The proteolytic activity of thermopsin was determined over a range of different temperatures using the synthetic hemoglobin as substrate. As shown in FIG. 1, the maximum activity is at 90° C. Further, residual activity is clearly detectable below 30° C., as shown in the inset of FIG. 1. At 100° C., the activity is still significant.

Thermostability of Thermopsin

Thermopsin is stable at 80° C. for 48 hours at pH 4.5 without appreciable loss of activity. The enzyme is also stable at approximately 4° C.

pH Dependence of Activity

Figure 2:
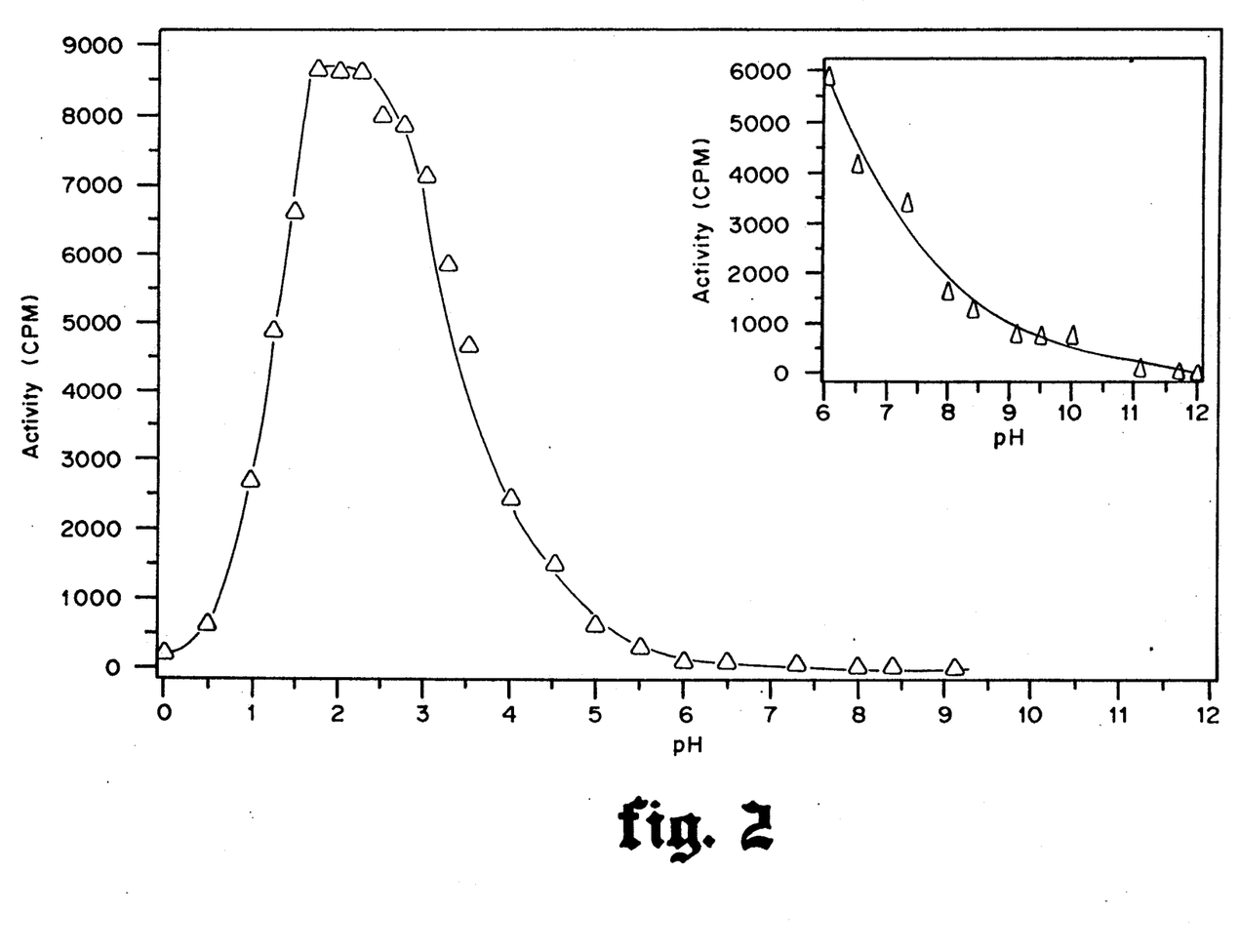
FIG. 2 is a graph of the pH dependence of the proteolytic activity of thermopsin. The inset figure shows the residual activity of thermopsin between pH 6 and pH 12. The buffers used for different pHs were: pH 0, 1M HCl; pH 0.5, 0.3M HCl; pH 1–3.5, 0.1M Na Citrate:HCl; pH 4.0, 0.1M NaOAc; pH 4.5, 0.1M 1-Methylpiperazine; pH 5.0, 0.1M NaOAc; pH 5.5, 0.1M L-Histidine; pH 6.0 and pH 6.5, 0.1M Bis-Tris HCl; pH 7.3, 0.1M HEPES; pH 8–9.1, 0.1M Tris; pH 9.5–11.1, 0.1M Na Borate; and pH 11.7, 0.1M $NaCO_3$. The assay was carried out at 40° C. since higher temperatures caused the substrate hemoglobin to precipitate at the lower pH values.

The primary activity of thermopsin ranges from pH 0.5 to pH 5, as shown in FIG. 2. The optimal activity is at approximately pH 2.0. Residual activity is clearly measurable in the pH range of 8 to 11 (FIG. 2, inset).

Effect of Inhibitors

The effect of various protease inhibitors on the activity of thermopsin was tested. As shown in Table II, pepstatin, the universal inhibitor for aspartic proteases, significantly inhibited thermopsin activity (50% inhibition at an inhibitor concentration of about 0.5 $\mu$M). The effects of other protease inhibitors are also shown in Table II. Thermopsin is not inactivated by DAN, an active site directed inhibitor for aspartic proteases (Rajagopalan, et al., *J. Biol. Chem.* 241, 4295-4297 (1966)). Compounds specific for thiol and metalloproteases, such as iodoacetic acid, N-ethylmaleimide, and EDTA have little effect. Two serine protease inhibitors, PMSF and TPCK, significantly inactivate thermopsin activity. The effect of TPCK may be related to thermopsin specificity for phenylalanine since N-p-Tosyl-1-lysine chloromethyl ketone (TLCK) is much less effective. The enzyme activity is also inhibited by NaAsO$_2$ and antipain.

TABLE II
Effects of Proteinase Inhibitors on Thermopsin

| Inhibitors | Concentration of Inhibitors in Preincubation (mM) | Enzyme Activity (%) |
|---|---|---|
| Pepstatin | 0.5 $\mu$M | 50 |
|  | 5 $\mu$M | 16 |
| DAN | 12 | 100 |
| NaAsO$_2$ | 2 | 28 |
| Iodoacetic Acid | 0.1 | 74 |
| N-ethylmaleimide | 0.1 | 95 |
| Aprotinin | 20 | 99 |
| Trypsin Inhibitor | 0.1 | 100 |
| PMSF | 2 | 28 |
| TPCK | 0.01 | 14 |
| TLCK | 0.01 | 78 |
| Leupeptin | 0.004 | 93 |
| Antipain | 0.02 | 25 |
| Elastatinal | 0.02 | 70 |
| EDTA | 1 | 100 |

Thermopsin is pre-incubated with the indicated level of inhibitor in 0.1 M phosphate buffer, pH 6.0, containing 1 mM EDTA and DTT at 37° C. for 5 min. Sodium formate (pH 3.2) and $^{14}$C-Hemoglobin is then added to a concentration as described above. The enzyme assay is then carried out at 80° C. for 15 min. Enzyme activity is expressed as percent of control.

Amino Acid Composition and Amino-Terminal Sequence

The amino acid composition of thermopsin is shown in Table III. The number of acidic residues (Asp+Asn=67; Glu+Gln=27) far exceeds that of basic residues (Lys and Arg, three residues each), indicating that thermopsin is an acidic protein. No histidine or cysteine was found. Using amino acid analysis for quantitation, the extinction coefficient of the enzyme at 280 nm was determined to be $1.1 \times 10^8$M$^{-1}$cm$^{-1}$ml$^{-1}$. The amino terminal sequence of thermopsin was found to be Tyr-Val-Asn-Pro-Tyr-.

Thermopsin Proteolytic Specificity

Thermopsin digests many protein substrates. Digestion of hemoglobin, ovalbumin, bovine serum albumin, and glyceraldehyde-3-phosphate dehydrogenase was monitored in SDS-polyacrylamide electrophoresis. These substrates are quickly degraded to smaller fragments and then presumably to smaller peptides that do not stain on the gel, indicating that thermopsin is an endopeptidase.

Figure 3A:
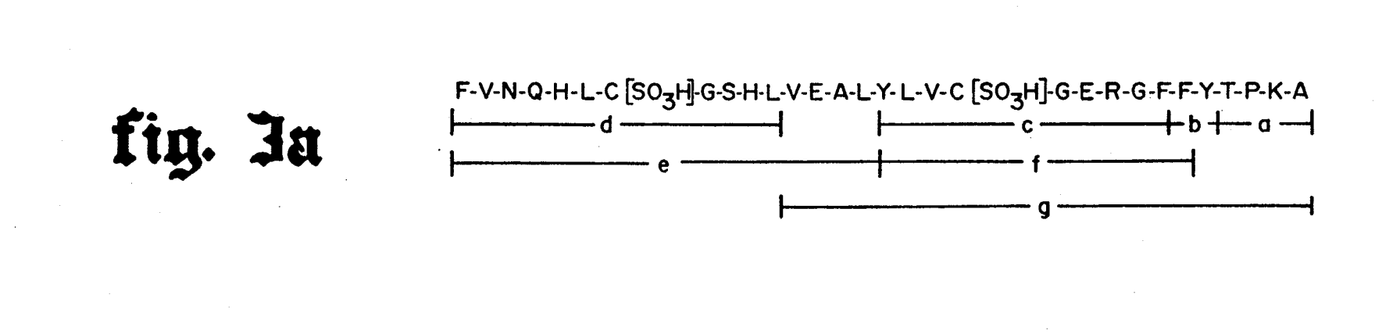
FIG. 3A is the HPLC profile of the separation of the peptides generated from the digestion of oxidized Insulin-B chain by thermopsin.

The specificity of thermopsin was studied using oxidized bovine Insulin B chain as substrate. Insulin-B chain was hydrolyzed with thermopsin at 80° C. in 0.1M sodium formate, pH 3.2. The resulting peptide fragments were then subjected to HPLC separation in a reversed phase column and the purified peptide fragments were analyzed for their amino acid compositions. FIG. 3a shows the HPLC separation of the peptide fragments of oxidized Insulin B chain from thermopsin digestion.

TABLE III
Amino Acid Composition of Thermopsin

| Amino Acid | Total nanomoles in sample | Residues per molecule |
|---|---|---|
| Asp | 89.8 | 67 |
| Thr | 62.8 | 47 |
| Ser | 56.2 | 42 |
| Glu | 37.0 | 27 |
| Gly | 65.4 | 48 |
| Ala | 44.0 | 33 |
| Val | 42.2 | 31 |
| Met | 10.4 | 8 |
| Ile | 41.9 | 31 |
| Leu | 53.4 | 40 |
| Tyr | 89.1 | 66 |
| Phe | 26.3 | 20 |
| Lys | 3.4 | 3 |
| Arg | 3.8 | 3 |
| Pro | 35.8 | 27 |
| Total Residues |  | 493 |

Figure 3B:
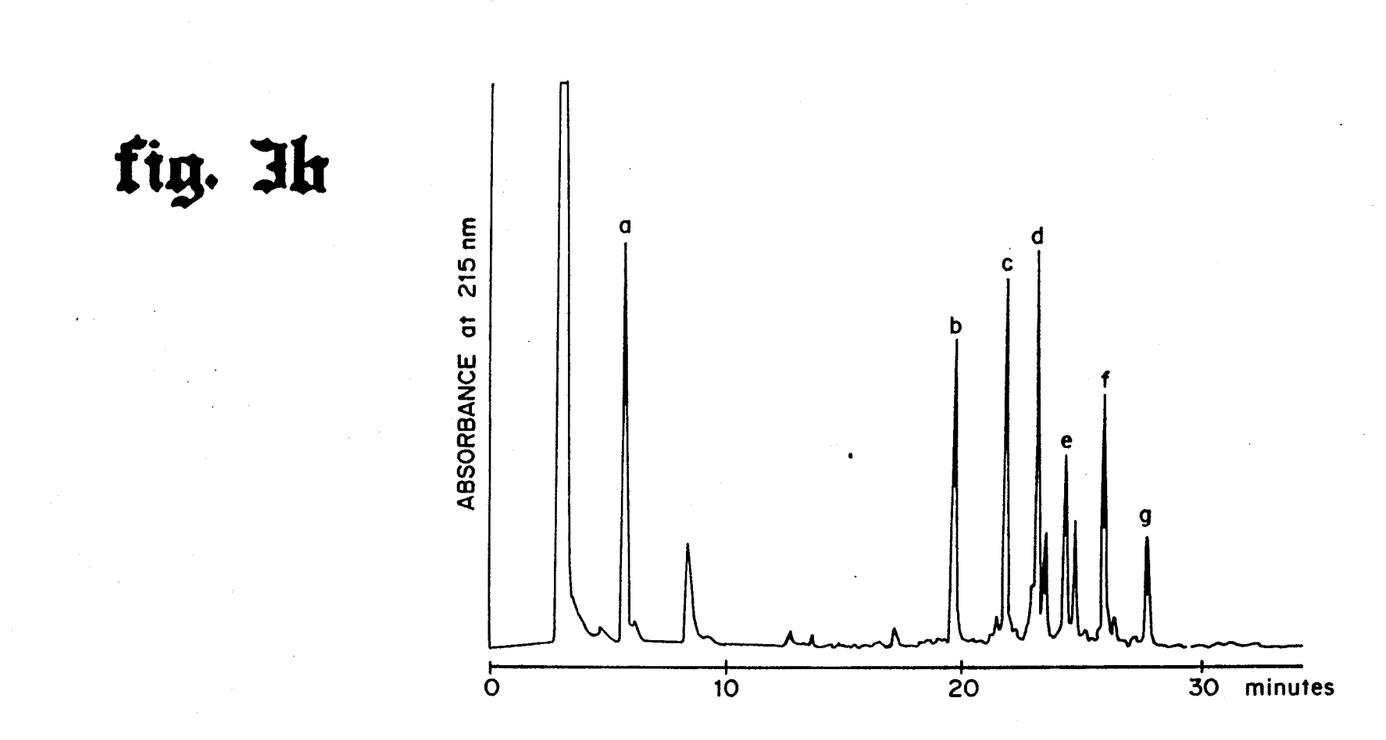
FIG. 3B summarizes the cleavage positions in Insulin-B chain by thermopsin.

Since the amino acid sequence of insulin B chain is known, the peptide fragments could be mapped to their original positions in the polypeptide and the cleavage specificity of thermopsin determined. The positions of cleavages are summarized in FIG. 3b. The hydrolysis of five bonds could be deduced: Leu-Val (res. 11-12), Leu-Tyr (res. 15-16), Phe-Phe (res. 24-25), Phe-Tyr (res. 25-26), and Tyr-Thr (res. 26-27).

These results establish that thermopsin is an endopeptidase with broad specificity which, in general, favors large hydrophobic residues on both sides of the scissile bond. This is confirmed using hydrolysis of a synthetic peptide Lys-Pro-Ala-Glu-Phe-Phe(NO$_2$)-Ala-Leu by thermopsin. A change of absorbance at 300 nm of this substrate upon the addition of the enzyme indicates that the hydrolysis takes place between Phe and Phe(NO$_2$) residues, which is confirmed by HPLC isolation of the hydrolytic products. HPLC results also indicate the absence of additional sites of hydrolysis on this substrate.

Kinetic Parameters

Figure 4:
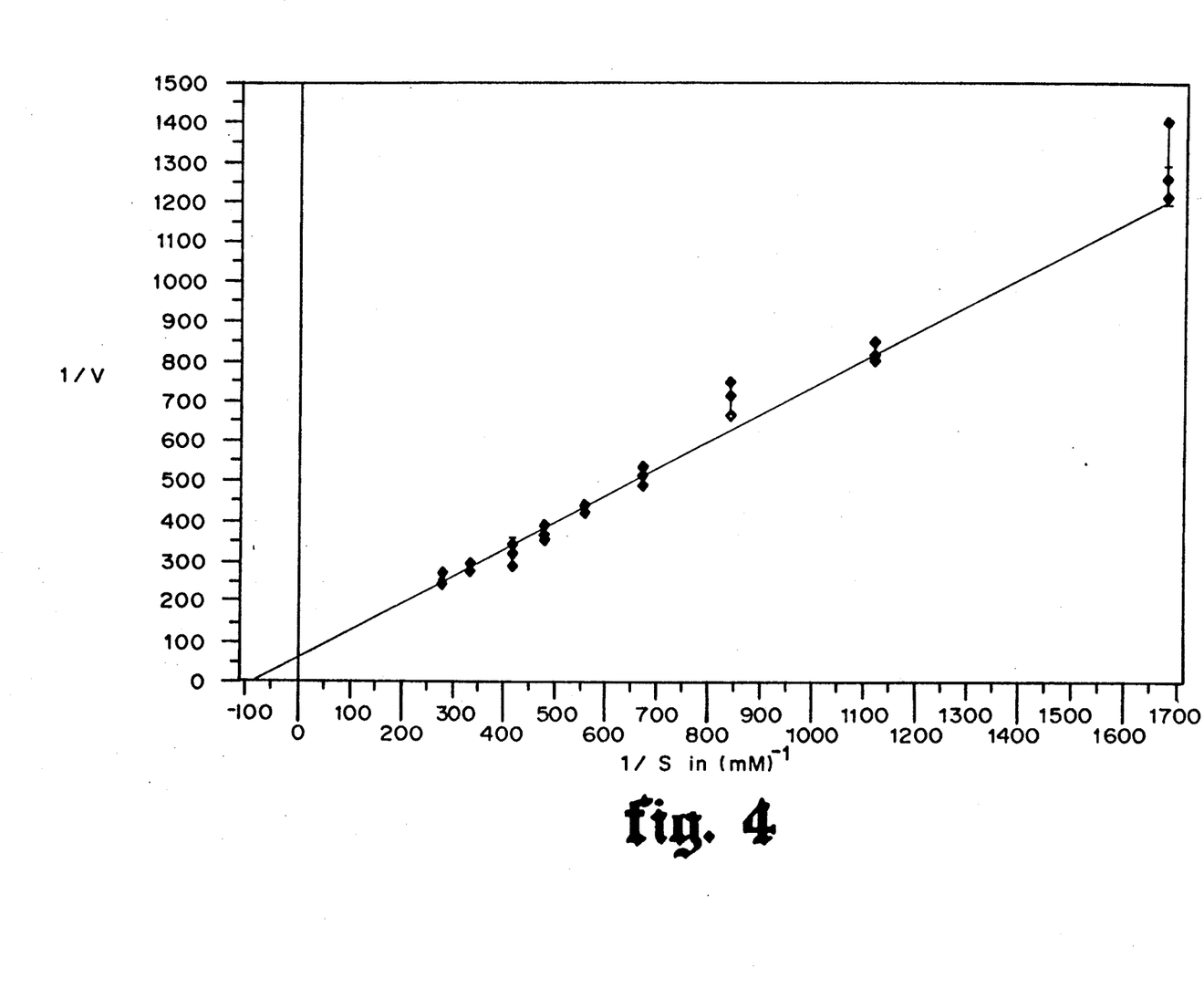
FIG. 4 is a Michaelis-Menten kinetic plot of thermopsin hydrolysis of methylated bovine hemoglobin. (♦) represent the actual data points at each substrate concentration (three determinations for each concentration) and the line was calculated by least-square analysis. The apparent Km is $1.2 \pm 0.2 \times 10^{-5}$M.

Thermopsin hydrolysis of hemoglobin follows Michael-Menten kinetics, as shown in the plot of FIG. 4. The mean Km value for methylated bovine hemoglobin is $1.2 \pm 0.2 \times 10^{-5}$M.

Cloning of the Thermopsin Gene

The thermopsin gene was cloned in order to (a) obtain sequence information for the thermopsin gene so as to deduce both the enzyme structure and the DNA control structures of the thermopsin gene, and (b) allow expression of the gene in recombinant expression systems for industrial and commercial applications. The techniques and methodologies are known to those skilled in the art, for example, as summarized below.

Since the genomes of archaebacteria are relatively small, it is easiest to clone the thermopsin gene directly from genomic DNA, for example, of *Sulfolobus acidocaldarius*, into a host such as *E. coli*, or other host cells including yeasts, fungi, and bacillus.

*S. acidocaldarius* cells are harvested from the cultural media by centrifugation and the genomic DNA is extracted and purified according to the method of Yeats, S., McWilliam, P., and Zillig, W., *EMBO Journal* 1: 1035–1038 (1982). The isolated DNA is digested with Sau3A and the resulting fragments, ranging from three to six kb, are recovered and sized by agarose gel electrophoresis. These sized fragments are then ligated with vectors such as pUC18, a commercially available vector, which have been previously digested with BamHI and treated with phosphatase to prevent self-ligation. The recombinant nucleic acid material is transformed into *E. coli* hosts such as strain DH5α, available without restriction from the American Type Culture Collection, Rockville, MD, to create a genomic library. This initial genomic library is amplified for storage.

Oligonucleotide probes for the thermopsin gene are synthesized according to the N-terminal amino acid sequence of the enzyme. Thermopsin can be fragmented using cyanogen bromide to generate more amino acid sequences for additional oligonucleotide probes. These fragments can be isolated by high performance liquid chromatography using reverse phase columns (Takahashi et al., *J. Biol. Chem.* 358:2819–2830, 1983; Jackson et al., *Biochemistry* 25: 108–114, 1986) and N-terminal amino acid sequences for each determined in a gas-phase protein sequencer. Oligonucleotide probes are based on both the lowest third codon degeneracy and the probability of the third codon utilization of other archaebacterial genes (Denta, et al., *J. Biol. Chem.* 263:6012–6015, 1988).

The *S. acidocaldarius* genomic library in *E. coli* is screened with the synthetic oligonucleotide probes for positive clones according to standard techniques (Maniatis, et al., *Molecular Cloning*, Cold Spring Harbor Laboratory, Cold Spring Harbor, N.Y., 1982). The *E. coli* cells containing the *S. acidocaldarius* genomic library can also be screened for the presence of the thermopsin promoter by screening for expression of the thermopsin gene using antibodies to thermopsin. Positive clones are selected on the basis of specific anti-thermopsin antibody binding.

A genomic library can also be prepared using the expression vector lambda gt11. Genomic DNA of *S. acidocaldarius* is sheared and sized; the resulting fragments are then methylated with EcoRI methylase, ligated to EcoRI linker sequences, digested with EcoRI and ligated into the EcoRI site of the lambda gt11 expression vector. The resulting phage library is screened with $^{125}$I-labelled antiserum directed against thermopsin using the method of Huynh, et al., in *DNA Cloning*, Vol. I, Clover ed., pp. 49–78 (IRL Press, Arlington, VA 1985).

Positive clones are further purified through secondary and tertiary screening, mapped with restriction enzymes, and sequenced with dideoxy chain termination DNA sequencing methods.

Expressing Cloned Thermopsin in Bacterial Hosts

Where the transcription and translation systems of *E. coli* recognize the promoter of thermopsin from *S. acidocaldarius*, the isolated thermopsin genomic clones can be used directly for expression. Alternatively, where the native promoter of thermopsin is not recognized by the *E. coli*, a large number of other *E. coli* and lambda phage promoters (e.g., trp. lac, tac, pL, and other promoters) can be used to direct the expression of thermopsin. These promoters can be engineered into commercially available vectors (such as pKK-223-3 from Pharmacia) along with the thermopsin gene in order to express the protein in *E. coli*. The synthesis of thermopsin in *E. coli* cytosol is possible since thermopsin enzymatic activity is low under these conditions (37° C. and neutral pH).

Alternatively, thermopsin can be expressed as a secretary protein which is transported out of the cell to the extracellular medium. Oligonucleotides of secretory leader sequences, such as that of omp (Ghrayeb, et al., *EMBO Journal* 3:2437–2442, 1984), are chemically synthesized and ligated in front of the thermopsin gene.

Digestion of insoluble proteins in the presence of SDS at low pH and high temperature In one embodiment of the present invention, thermopsin is used to digest insoluble proteins. Proteins that are denatured tend to aggregate and form insoluble precipitates which are generally inaccessible to, and not digested by, proteases. The addition of a detergent, such as sodium dodecyl sulfate (SDS), solubilizes these protein precipitates and facilitates access of the protease to the protein. Most proteases are, however, sensitive to and inactivated by detergents. Thermopsin, in addition to being thermostable, is relatively resistant to SDS, even at high concentration levels (3% w/v), as shown by the following study.

Four proteins, bovine serum albumin (BSA), ovalbumin, glyceraldehyde-3-Phosphate dehydrogenase (G-3-DH), and carbonic anhydrase, were dissolved in 20 $\mu$M tris-HCl, pH 8.0 at a concentration of 2 mg protein/90 $\mu$l buffer. Each solution was heated at 100° C. for 10 minutes to denature and precipitate the protein. After cooling to room temperature, 10 $\mu$l of 10% (w/v) SDS was added to solubilize the protein precipitates. Five $\mu$l aliquots of each solubilized protein solution were mixed with thermopsin, SDS, and 0.1M sodium formate (pH 3.2) buffer to a final volume of 50 $\mu$l. The SDS concentration was varied from 0.1% to 4.1%. The solutions were then incubated at 80° C. for 30 min., followed by SDS-polyacrylamide electrophoresis to monitor digestion. Thermopsin digested all 4 proteins, even in the presence of SDS at concentrations ranging from 0.1% to 3.1%. Thermopsin is clearly resistant to inactivation by SDS, even at concentrations up to 3.1%, and can therefore be used in conjunction with detergent to digest and remove insoluble protein contaminants.

Modifications and variations of the present invention, a thermostable acid protease and methods for use thereof, will be obvious to those skilled in the art from the foregoing detailed description. Such modifications and variations are intended to come within the scope of the appended claims.

We claim:

1. An isolated thermostable, aspartic protease,
    wherein enzymatic activity is measurable at a temperature between 0° C. and 100° C. and a pH between 0 and 11;
    wherein the enzyme or fragment thereof hydrolyzes the following bonds: Leu-Val, Leu-Tyr, Phe-Phe, Phe-Tyr, and Tyr-Thr;
    wherein the enzyme or fragment thereof is inhibited by pepstatin, PMSF, TPCK, antipain, and $NaAsO_2$ but not by DAN or inhibitors of thiol and metalloproteases; and wherein the protease is expressed by an archaebacteria.

2. The protease of claim 1 expressed by an archaebacteria selected from the group consisting of *Sulfolobus acidocaldarius*, *Sulfolobus solfataricus*, and *Thermoplasma acidophilum*.

3. The protease of claim 1 purified to homogeneity by chromatography on DEAE-agarose gel, phenyl-agarose gel, acrylamide gel, followed by FPLC, and HPLC.

4. The protease of claim 1 having maximum enzymatic activity at temperatures ranging from 85° C. to 100° C.

5. The protease of claim 1 having maximum enzymatic activity at pH 2.

* * * * *